United States Patent [19]

Yamaguchi et al.

[11] Patent Number: 4,803,258

[45] Date of Patent: Feb. 7, 1989

[54] THERMOPLASTIC AROMATIC POLYETHER-PYRIDINE AND PROCESS FOR PREPARING SAME

[75] Inventors: Keizaburo Yamaguchi, Kawasaki; Hideaki Oikawa, Yokohama; Kenichi Sugimoto, Yokohama; Masahiro Ohta, Yokohama; Akihiro Yamaguchi, Kamakura, all of Japan

[73] Assignee: Mitsui Toatsu Chemicals, Incorporated, Tokyo, Japan

[21] Appl. No.: 76,873

[22] Filed: Jul. 23, 1987

[30] Foreign Application Priority Data

Aug. 1, 1986 [JP] Japan ................................. 61-180180
Nov. 6, 1986 [JP] Japan ................................. 61-262856

[51] Int. Cl.$^4$ ............................................. C08G 65/40
[52] U.S. Cl. ................................... 528/211; 528/125; 528/128; 528/210
[58] Field of Search ................ 528/211, 210, 125, 128

[56] References Cited

FOREIGN PATENT DOCUMENTS 2826684 1/1979 Fed. Rep. of Germany .
2826685 1/1979 Fed. Rep. of Germany .
0061913 10/1982 European Pat. Off. .

*Primary Examiner*—Harold D. Anderson
*Attorney, Agent, or Firm*—Oblon, Fisher, Spivak, McClelland & Maier

[57] ABSTRACT

Disclosed are thermoplastic aromatic polyetherpyridines composed of repeating structural units each containing one or more pyridine rings. These polymers are prepared by reacting a 2,6-dihalogenopyridine with one or two dihydroxy compounds or by reacting a bis(6-chloro-2-pyridyloxy) compound with a dihydroxy compound. The polymers thus obtained have an excellent combination of heat resistance, moldability and other properties, and hence are useful in a wide variety of applications.

5 Claims, No Drawings

THERMOPLASTIC AROMATIC POLYETHER-PYRIDINE AND PROCESS FOR PREPARING SAME

BACKGROUND OF THE INVENTION

1. Field of the Invention

This invention relates to thermoplastic aromatic polyether-pyridines and a process for preparing such polymers.

These thermoplastic aromatic polyether-pyridines (hereinafter referred to as PEPs) are thermoplastic resins characterized in that each of their repeating structural units contains one or more pyridine rings and two or more oxygen linkages.

These PEPs have wide applications including molding materials, films, insulating materials for wire coating use, and the like. Moreover, it is expected that electrical conductivity can be imparted thereto by doping the nitrogen atom of the pyridine rings with a metal ion. Furthermore, the PEPs of the present invention are also very useful as functional polymeric materials, because hollow fibers or thin membranes formed of these PEPs have the ability to retain or separate certain cations and are useful as polymeric catalysts for polymer reactions.

2. Description of the Prior Art

No polyether resins composed of repeating structural units each containing a pyridine ring have been known in the prior art.

The present inventors have for the first time developed such unique polyether resins and a process for preparing them.

Conventionally, common aromatic polyether resins have been prepared by condensing an aromatic bisphenol with an aromatic dihalogeno compound. For example, a polyether-ketone resin has been prepared from hydroquinone and 4,4'-difluorobenzophenone (Japanese Patent Laid-Open No. 90296/'79) and a polyether-sulfone resin had been prepared from 4,4'-dihydroxydiphenyl sulfone and 4,4'-dichlorodiphenyl sulfone (Japanese Patent Laid-Open No. 27500/'77).

In these well-known processes, however, the preparation of aromatic polyether resins is possible only when an aromatic dihalide compound whose two halogen atoms are activated by an electron attractive group such as a carbonyl or sulfonyl group located at the para position (e.g., 4,4'-difluorobenzophenone or 4,4'-dichlorodiphenyl sulfone) is used as a starting material.

Meanwhile, an attempt has been made to utilize p-difluorobenzene and p-dibromobenzene that have two halogen atoms on the same benzene ring and exhibit relatively high reactivity. However, these compounds do not have sufficient activity to be useful as starting materials for polycondensation reaction, so that no success has been attained in the preparation of resins having a high degree of condensation.

Moreover, condensation polymers derived from para-substituted monomers and hence having a linear molecular configuration, such as the above-described polyether resins, are so rigid that their fluidity is insufficient for molding purposes. In order to obtain better fluidity, there is a need for resins having a nonlinear molecular configuration and, therefore, ones derived from meta-substituted monomers.

Furthermore, with regard to the performance aspect of heat-resistant resins, it is desirable that they have excellent functional properties other than heat resistance. Thus, there is a need for heat-resistant resins which exhibit excellent moldability and other functional properties and/or can be provided with certain electrical properties such as electrical insulating or conductive properties.

SUMMARY OF THE INVENTION

In view of the above-described state of the art and industrial demands, the present inventors have made an attempt to develop novel functional resins and have also made an exhaustive study of the method for preparing such resins and the monomer used for this purpose. As a result, they have found that a novel resin can be obtained by using a meta-substituted aromatic dihalide compound having two halogen atoms located at the meta positions of a single aromatic ring. More specifically, it has unexpectedly been found that a stable aromatic polyether resin containing heterocyclic rings at a high degree of condensation can be obtained by using a 2,6-dihalogenopyridine as a starting material and condensing it with a dihydroxy compound, and that this resin has a variety of useful functional properties. The present invention has been completed on the basis of this discovery.

The present inventors have also found that the reactivity of such a 2,6-dihalogenopyridine (e.g., 2,6-dichloropyridine) differs markedly between the first-reacting and the second-reacting chlorine atom and, therefore, a bis(6-chloro-2-pyridyloxy) compound can be prepared by reacting only one chlorine atom of 2,6-dichloropyridine with a dihydroxy compound.

Such a bis(6-chloro-2-pyridyloxy) copound can be reacted with a dihydroxy compound to prepare a polyether-pyridine resin. In this case, an alternating condensation polyether resin can also be prepared by condensing a bis(6-chloro-2-pyridyloxy) compound with a dihydroxy compound which is different from that used in the preparation of the bis(6-chloro-2-pyridyloxy) compound. The resin so prepared has additional unique properties and may be expected to find new uses.

Thus, the present invention relates to novel thermoplastic aromatic polyether-pyridines obtained by condensing a 2,6-dihalogenopyridine, which is an active meta-substituted aromatic dihalide compound, or a bis(6-chloro-2-pyridyloxy) compound with a dihydroxy compound, as well as a process for preparing such polymers.

More specifically, the present invention provides a thermoplastic aromatic polyether-pyridine composed of repeating structural units of the general formula

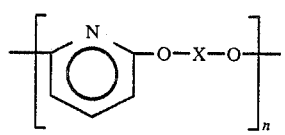 (1)

where X is a divalent radical selected from the group consisting of

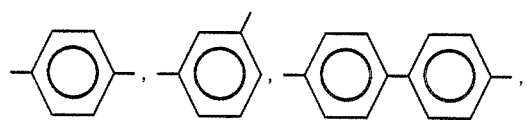

-continued

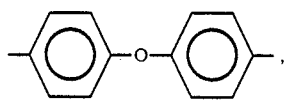

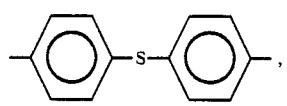

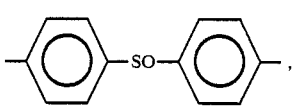

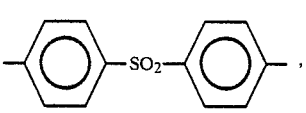

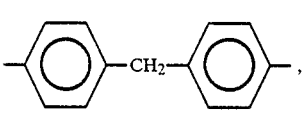

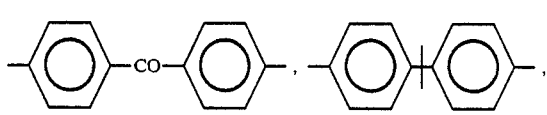

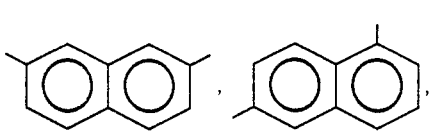

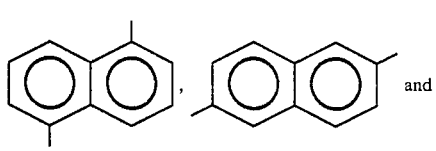 and

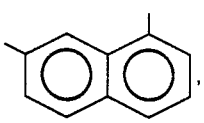

one or two types of such divalent radicals are present in the molecule, and n represents a degree of polymerization and is a whole number of 10 or greater.

The present invention also provides a process for preparing such a thermoplastic aromatic polyetherpyridine which comprises (A) (a) mixing a 2,6-dihalogenopyridine of the general formula

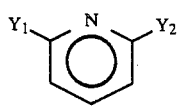 (2)

where $Y_1$ and $Y_2$ are chlorine, bromine or fluorine atoms and may be the same or different, with one or two or more dihydroxy compounds of the general formula

HO—X—OH (3)

where X is as defined for the general formula (1), in a substantially equimolar ratio, or (b) mixing a bis(6-chloro-2-pyridyloxy) compound of the general formula

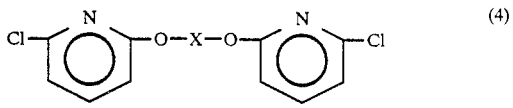 (4)

where X is as defined for the general formula (1), which has been obtained by reacting 2,6-dichloropyridine with a dihydroxy compound of the general formula (3) in the presence of a base in an aprotic polar solvent, with a dihydroxy compound of the general formula (3) in a substantially equimolar ratio, and (B) effecting polycondensation of these reactants under substantially water-free conditions in the presence of an alkali metal carbonate and/or bicarbonate or an alkali metal hydroxide.

DETAILED DESCRIPTION OF THE PREFERRED EMBODIMENTS

The novel thermoplastic aromatic polyetherpyridines of the present invention have a degree of polymerization (i.e., a whole number represented by n) of 10 or greater and preferably 50 to 3,000.

Their repeating structural units can vary widely according to the types of monomers used as the starting materials. Where a 2,6-dihalogenopyridine of the general formula (2) and only one dihydroxy compound of the general formula (3) are used as the starting materials, there is obtained a thermoplastic aromatic polyether-pyridine of the general formula (1) in which the divalent radicals represented by X are all the same. Moreover, a block or random copolymer is produced by using two or more dihydroxy compounds. Furthermore, an alternating cocondensation product is obtained by effecting cocondensation of a bis(6-chloro-2-pyridyloxy) compound and a dihydroxy compound.

Since these polyether-pyridines are formed, for the most part, by ether linkages, they are stable to heat and various atmospheres.

While the previously described conventional aromatic polyether resins have a linear molecular configuration owing to the chemical structures of the compounds used as the starting materials, the PEPs of the present invention have a folded molecular configuration. More specifically, in the practice of the present invention, a 2,6-dihalogenopyridine compound is used as a starting material. This compound has a pair of halogen atoms located at the meta positions, so that the resulting resin has a folded molecular configuration instead of a linear one. Moreover, any desired folded molecular configurations can be obtained by using it in combination with various diphenols. For example, the repeating structural units have the meta-para structure when hydroquinone or 4,4'-bisphenol is used as the diphenol, and they have the meta-meta structure when resorcinol or 2,7-dihydroxynaphthalene is used as the diphenol.

The above-described choice of the molecular configuration is important in that this permits various properties, such as crystallinity, toughness, flexibility, adhesive properties and the like, to be properly controlled according to the intended purpose.

Thus, the PEPs of the present invention are novel resins composed of repeating structural units having a nitrogen atom in the aromatic nucleus and are characterized by a variety of highly functional properties.

The present inventors have succeeded in preparing such novel resins with attention focused on the reactivity of the 2,6-dihalogenopyridine compound used as a starting material. The resins so prepared are characterized by having one or more pyridine rings in each repeating structural unit and two or more oxygen linkages per pyridine ring. Moreover, it is also possible to prepare alternating condensation polymers composed of two different types of repeating structural units. Furthermore, their properties can be diversely modified by the combined use of various diphenols. For example, when a bis(6-chloro-2-pyridyloxy) compound derived from a para-dihydroxy compound is used in combination with a meta-dihydroxy compound, the resulting resin is reduced in glass transition temperature and toughness, but improved in flexibility and adhesive properties, as compared with the resin obtained by using the para-dihydroxy compound alone.

The process of the present invention will more specifically be described hereinbelow.

The 2,6-dihalogenopyridine of the general formula (2), which is used as one of the two starting materials, is selected from the group consisting of 2,6-dichloropyridine, 2-bromo-6-chloropyridine, 2,6-dibromopyridine, 2 chloro-6-fluoropyridine, 2-bromo-6-fluoropyridine and 2,6-difluoropyridine. Among them, 2,6-dichloropyridine is preferred for industrial purposes. The bis(6-chloro-2-pyridyloxy) compound of the general formula (4), which is also used as one of the two starting materials, is obtained by condensing 2,6-dichloropyridine with a diphenol. Specific examples of the bis(6-chloro-2-pyridyloxy) compound include 2,2-bis[4-(6-chloro-2-pyridyloxy)]propane, 4,4-bis(6-chloro-2-pyridyloxy)diphenyl sulfide, 1,4-bis(6-chloro-2-pyridyloxy)benzene, 1,3-bis(6-chloro-2-pyridyloxy)benezene, 1,6-bis(6-chloro-2-pyridyloxy)naphthalene, 1,5-bis(6-chloro-2-pyridyloxy)naphthalene, 2,6-bis(6-chloro-2-pyridyloxy)naphthalene, 2,7-bis(6-chloro-2-pyridyloxy)naphthalene, 1,7-bis(6-chloro-2-pyridyloxy)naphthalene, 4,4'-bis(6-chloro-2-pyridyloxy)benzophenone, 4,4'-bis(6-chloro-2-pyridyloxy)diophenylmethane, 4,4'-bis(6-chloro-2-pyridyloxy)diphenyl sulfone, 4,4'-bis(6-chloro-2-pyridyloxy)diphenyl sulfoxide, 4,4'-bis(6-chloro-2-pyridyloxy)diphenyl ether, 4,4'-bis(6-chloro-2-pyridyloxy)diphenyl and the like.

Among these compounds, 2,6-dihalogenopyridines can be prepared by halogenating pyridine according to conventional procedure [as described in Dai-Yuki-Kgaku (Asakura Shoten), Vol. 16, p. 20]. Moreover, the mono- and difluoropyridines can also be prepared by reacting other halogenopyridines with potassium fluoride or the like to exchange fluorine for the other halogen atom(s).

On the other hand, bis(6-chloro-2-pyridyloxy) compounds can be prepared according to the following procedure which has been developed by the present inventors.

Specifically, they can be prepared by reacting 2,6-dichloropyridine with a dihydroxy compound of the general formula

HO—X—OH (3)

where X is a divalent radical selected from the group consisting of

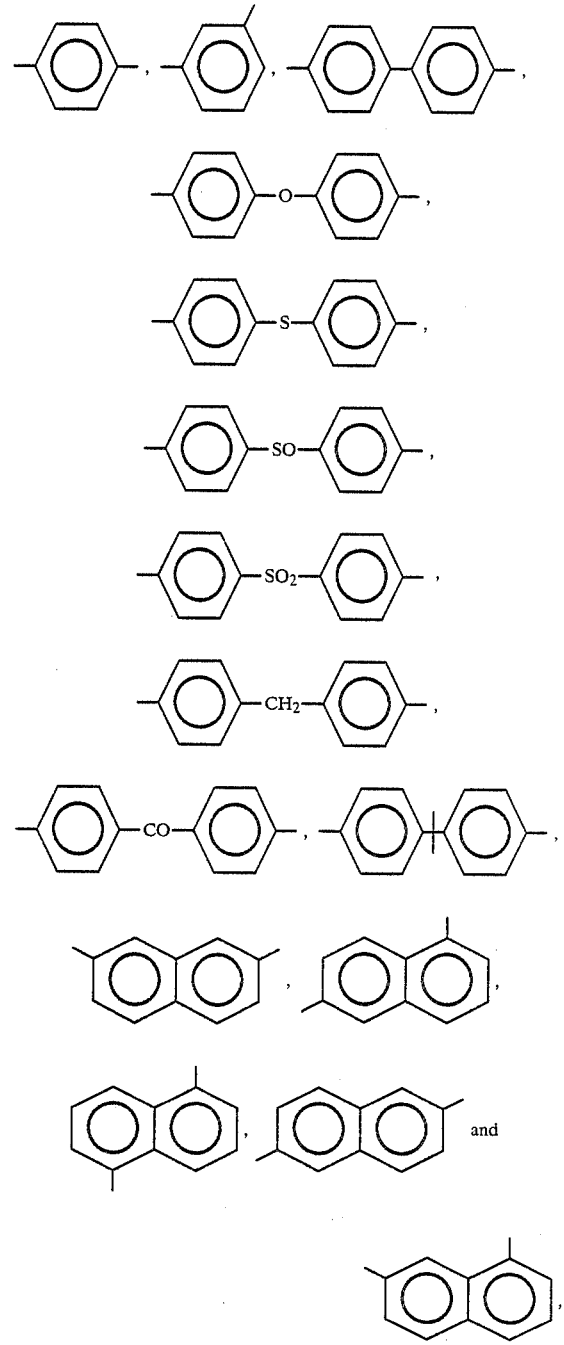

in the presence of a base in an aprotic polar solvent.

The dihydroxy compound used in this procedure can be any of the dihydroxy compounds useful in the preparation of the resins of the present invention as will be described later.

In this procedure, 2,6-dichloropyridine and the dihydroxy compound are used in such a proportion that 2 moles or more, preferably 2 to 3 moles, of 2,6-dichloropyridine is present for each mole of the dihydroxy compound. The base is selected from the group consisting of hydroxides, carbonates, bicarbonates and alkoxides of alkali metals. Specific examples of useful bases include potassium hydroxide, sodium hydroxide, lithium hydroxide, potassium carbonate, sodium carbonate, lithium carbonate, potassium bicarbonate, sodium bicarbonate, lithium bicarbonate, potassium ethoxide, potassium isopropoxide, sodium methoxide, lithium ethoxide and the like. Among them, the hydroxide and carbonate of potassium or sodium are preferred. It is to be understood that these bases may be used alone or in admixture of two or more. The base is used in an amount of one or more equivalents, preferably 1 to 1.5 equivalents, per equivalent of the hydroxyl groups of the dihydroxy compound used as a starting material.

The reaction is carried out in a solvent. An aprotic polar solvent is used for this purpose. Specific examples of useful aprotic polar solvents include N-methylformamide, N,N-dimethylformamide, N-methylpyrrolidone, N,N-dimethylacetamide, 1,3-dimethyl-2-imidazolidinone, dimethyl sulfoxide, hexamethylphosphoric triamide, dimethyl sulfone, sulfolane and the like. Although no particular limitation is placed on the amount of solvent used, it is usually used in an amount of 1 to 10 times the weight of the starting materials. In carrying out the reaction, a quaternary ammonium salt, a quaternary phosphonium salt, a macrocyclic polyether such as Crown Ether, a nitrogen-containing macrocyclic polyether such as Criptate, a nitrogen-containing chain polyether such as tris(3,6-dioxoheptyl)amine, a polyethylene glycol dialkyl ether or the like may be added to the reaction system for the purpose of allowing the reaction to proceed more smoothly.

The reaction is carried out at a temperature of 80° to 160° C. and preferably 100° to 140° C. After completion of the reaction, the reaction mixture is cooled and the crystals which separated out during the reaction or have separated out as a result of cooling can be obtained by filtration.

The other starting material used in the process of the present is a dihydroxy compound of the general formula (3). Specific examples of useful dihydroxy compounds include hydroquinone, resorcinol, 4,4'-dihydroxybiphenyl, 4,4'-dihydroxydiphenyl ether, 4,4'-thiodiphenol, 4,4'-dihydroxydiphenyl sulfoxide, 4,4'-dihydroxydiphenyl sulfone, 4,4'-dihydroxydiphenylmethane, 4,4'-dihydroxybenzophenone, 2,2'-bis(4-hydroxyphenyl)propane, 2,7-dihydroxynaphthalene, 1,6-dihydroxynaphthalene, 1,5 dihydroxynaphthalene, 2,6-dihydroxynaphthalene, 1,7-dihydroxynaphthalene and the like.

In preparing the resins of the present invention, one or two or more dihydroxy compounds as defined above may be used where the other starting monomer is a 2,6-dihalogenopyridine. Where a bis(6-chloro-2-pyridyloxy) compound is used as the other starting monomer, the dihydroxy compound used for this purpose can be the same as that used in the preparation of the bis(6-chloro 2-pyridyloxy) compound. However, a different dihydroxy compound is usually used to produce an alternating condensation polymer having unique properties.

In order to prepare the resins of the present invention, the above-defined 2,6-dihalogenopyridine or bis(6-chloro-2-pyridyloxy) compound and the above-defined dihydroxy compound should be reacted in a substantially equimolar ratio. As used herein, the term "substantially equimolar ratio" means that the amount of the aforesaid dihalogenopyridine or dihydroxy compound may exceed its stoichiometric amount by about 10% or less. The use of a slight excess of one reactant serves to retard the reaction and thereby control the molecular weight of the resulting polycondensation product.

The PEPs of the present invention can have varying degrees of crystallinity depending on the type of the dihydroxy compound used. For example, PEPs obtained by using hydroquinone, 4,4'-dihydroxybiphenyl or a dihydroxynaphthalene as a starting material are highly crystalline polymers and are hardly soluble or insouble in most solvents. It is another feature of the present invention that, for the purpose of controlling the degree of crystallinity or for other purposes, a suitable combination of dihydroxy compounds can be used to effect co-condensation and thereby change the degree of crystallinity according to the intended purpose.

Where co-condensation is effected by using two dihydroxy compounds, these dihydroxy compounds may be used in a molar ratio ranging from 5:95 to 95:5.

In the polycondensation process of the present invention, an alkali metal carbonate, bicarbonate or hydroxide is used as the base. In the case of alkali metal hydroxides such as sodium hydroxide and potassium hydroxide, it is necessary to use them in an exactly defined stoichiometric amount and, moreover, it is rather difficult to attain a satisfactorily high degree of condensation. This seems to be due to the occurrence of side reactions (e.g., hydrolysis of the dihalide compound) in the presence of excess alkali metal hydroxide [see, for example, Polymer, Vol. 25, 1827–1836 (1984)]. In addition, the water present in the reaction system must be removed completely. For this reason, the preferred bases for use in the present invention are alkali metal carbonates and bicarbonates. Specific examples of useful alkali metal carbonates and bicarbonates include potassium carbonate, sodium carbonate, cesium carbonate, rubidium carbonate, potassium bicarbonate, sodium bicarbonate and the like. Among them, potassium carbonate and sodium carbonate are preferably used for industrial purposes. It is to be understood that these two carbonates may be used in admixture and they may also be used in combination with other carbonates or bicarbonates.

The total amount of these alkali metal salts should preferably be such that not less than two gram atoms of alkali metal is present for each mole of the dihydroxy compound and, in other words, not less than one alkali metal atom is present for each hydroxyl group. If the amount is smaller, the degree of condensation will be reduced. On the other hand, a large excess of alkali metal carbonate and/or bicarbonate should not be used so as to avoid undesirable side reactions. It is most preferable to use them in such an amount as to provide 1 to 1.2 alkali metal atoms for each hydroxyl group.

The process of the present invention can be carried out in the manner described in Japanese Patent Publication No. 7959/'78. That is, the starting materials can be reacted in a stirred and mixed state without using any solvent. However, it is preferable for industrial purposes to carry out the reaction in the presence of a solvent.

To this end, aprotic polar solvents are preferably used. Specific examples of such solvents include 1,3-dimethyl-2-imidazolidinone, hexamethylphosphoramide, formamide, N-methylformamide, N,N-dimethylformamide, N,N-diethylformamide, acetamide, N-methylacetamide, N,N-dimethylacetamide, N,N,N',N'-tetramethylurea, 2-pyrrolidone, N-methylpyrrolidone, dimethyl sulfoxide, dimethyl sulfone, sulfolane and the like. Among them, 1,3-dimethyl-2-imidazolidinone, N-methylpyrrolidone, dimethyl sulfone and sulfolane are especially preferred.

These solvents are usually used in an amount of about 0.5 to 10 times the weight of the starting materials.

The reaction temperature can range from 90° to 300° C. and preferably 120° to 250° C. It is preferable to carry out the reaction by heating the reaction mixture stepwise.

In order to allow the reaction to proceed more smoothly, a macrocyclic polyether such as Crown Ether, a nitrogen-containing macrycyclic polyether such as Criptate, a nitrogen-containing chain polyether such as tris(3,6-dioxoheptyl)amine or a polyethylene glycol dialkyl ether may be used as an interphasic moving catalyst.

The polycondensation reaction using the above-defined starting materials and other agents is usually carried out in the following manner: Predetermined amounts of a 2,6-dihalogenopyridine or a bis(6-chloro-2-pyridyloxy) compound, a dihydroxy compound, a base and a solvent are charged into a reactor. Moreover, a suitable solvent such as benzene, toluene or chlorobenzene is added thereto for the purpose of removing any water from the reaction system. This solvent serves as an azeotropic agent for continuously and qucikly removing the water present in the reaction system and the water formed therein during the reaction, and has the effect of producing a polymer having a high degree of condensation.

The reaction is carried out by heating the reaction mixture stepwise while passing therethrough an inert gas such as nitrogen, argon, helium, carbon dioxide or the like. At the initial stage of the reaction, a suitable solvent is distilled for the purpose of water removal. Finally, the temperature is raised to about 200°-250° C. before completion of the reaction.

The reaction time ranges approximately from 4 to 20 hours.

After completion of the reaction, the reaction mixture may be treated according to any conventional procedure for the recovery of polymers. Specifically, the reaction mixture may be poured into methanol, water or the like to precipitate the polymer. Alternatively, where the polymer is soluble in halogenated hydrocarbon solvents, it is also possible to dilute the reaction mixture with such a solvent, remove the inorganic salt and the reaction solvent therefrom by extraction with water, separate the organic phase, and precipitate the polymer by pouring it into methanol or the like.

The PEPs of the present invention are novel thermoplastic aromatic polyether resins composed of repeating structural units each containing one or more pyridine rings. These resins have excellent heat resistance and moldability, can be produced at low cost, and may be expected to exhibit new combinations of properties attributable to the nitrogen atom of the pyridine rings. Accordingly, they are useful in a wide variety of applications. The provision of such novel and useful resins is believed to contribute to the development of the art and hence have great significance.

The present invention is further illustrated by the following examples.

The viscosities of the polymers obtained in Examples 1–7 and the results of their thermal analysis are shown in Table 1, and their flow characteristics are shown in Table 2. The same characteristics of the polymers obtained in Examples 8–17 are shown in Table 4. These characteristics.were determined according to the procedures described below.

Inherent viscosity ($\eta_{inh}$) was calculated from the following equation.

$$\eta_{inh} = \ln(t/t_0)/C$$

where ln is a natural logarithm, t is the flowing time (in seconds) at 35° C. of a solution of 0.5 g of an aromatic polyether-pyridine in 100 ml of a solvent mixture composed of phenol and tetrachloroethane (in a weight ratio of 6:4), $t_0$ is the flowing time (in seconds) at 35° C. of the aforesaid solvent mixture alone, and C is the concentration (in g/dl) of the solution to be tested.

Glas transition temperature (Tg) and melting point (Tm) were measured according to the DSC method, and 5% thermal weight loss temperature ($Td_5$) was measured in air according to the DTA-Tg method.

Degree of crystallinity was determined according to the X-ray diffraction (XRD) method.

Flow characteristics were measured with a flow tester (Model CFT-500; manufactured by Shimazu Seisakusho). Measurements were made at a given temperature and under a given load, using a die length of 10 mm, a die diameter of 1 mm, a preheating time of 5 minutes, and a measuring range of depression of 3–7 mm.

EXAMPLE 1

Into a 100-ml flask fitted with a stirrer and a water separator were charged 11.42 g (0.05 mole) of purified 2,2′-bis(4-hydroxyphenyl)propane, 7.5 g (0.0503 mole) of 2,6-dichloropyridine, 7.6 g (0.055 mole) of anhydrous potassium carbonate, 25 ml of 1,3-dimethyl-2-imidazolidinone and 20 ml of benzene. By heating this reaction mixture with stirring while passing nitrogen gas therethrough, water was azeotropically removed under the reflux of benzene for an hour. Subsequently, while the reflux was continued, the benzene was gradually expelled from the reaction system and the temperature was raised from 120° C. to 140° C. over a period of 2 hours. Then, after the temperature was further raised to 170°-180° C., the reaction was continued for 3 hours with the removal and distillation of water by occasional addition of toluene. Thereafter, the reaction was continued at 200° C. for 3 hours and then at 220° C. for 3 hours. On completion of the reaction, the resulting viscous resin solution was cooled and dissolved in 150 ml of methylene chloride. Using a separatory funnel, this methylene chloride solution was extracted twice with 300-ml portions of water. Then, the methylene chloride solution was added dropwise to 800 ml of methanol stirred vigorously in a high-speed mixer. After completion of the addition, the stirring was continued for an additional 10 minutes and the resulting white precipitate was separated by filtration. This white precipitate was resuspended in 300 ml of a 70% aqueous solution of methanol, followed by stirring. Thereafter, the white precipitate was separated by filtration, washed with water and then dried to obtain 14.5 g of a polymer in the form of white powder.

EXAMPLE 2

The procedure of Example 1 was repeated except that 11.9 g (0.05 mole) of 2,6-dibromopyridine, 10.91 g (0.05 mole) of 4,4′-thiodiphenol, 7.6 g (0.055 mole) of anhydrous potassium carbonate and 20 ml of sulfolane were used in the reaction mixture. Thus, there was obtained 13.8 g of a white polymer.

EXAMPLE 3

Reaction was carried out in the same manner as described in Example 1, except that 7.5 g (0.0503 mole) of 2,6-dichloropyridine, 9.31 g (0.05 mole) of 4,4'-dihydroxydiphenyl, 7.6 g (0.055 mole) of anhydrous potassium carbonate and 20 ml of 1,3-dimethyl-2-imidazolidinone were used in the reaction mixture. On completion of the reaction, crystals ha precipitated from the reaction mixture. Thus, the reaction mixture was directly poured into 400 ml of methanol, followed by stirring in a high-speed mixer for 10 minutes. The crystals were separated by filtration and resuspended in 400 ml of a 70% aqueous solution of methanol, followed by stirring. Thereafter, the crystals were separated by filtration, washed thoroughly with water and then dried to obtain 13.0 g of a polymer in the form of white powder.

EXAMPLE 4

The procedure of Example 3 was repeated except that 5.8 g (0.05 mole) of 2,6-difluoropyridine, 5.5 g (0.05 mole) of hydroquinone, 5.51 g (0.052 mole) of anhydrous potassium carbonate and 20 ml of 1,3-dimethyl-2-imidazolidinone were used in the reaction mixture. Thus, there was obtained 9.0 g of a white polymer.

EXAMPLE 5

The procedure of Example 3 was repeated except that 7.5 g (0.0503 mole) of 2,6-dichloropyridine, 5.5 g (0.05 mole) of resorcinol, 7.6 g (0.055 mole) of anhydrous potassium carbonate and 20 g of dimethyl sulfone were used in the reaction mixture. Thus, there was obtained 8.6 g of a white polymer.

EXAMPLE 6

The procedure of Example 3 was repeated except that 8.01 g (0.05 mole) of 2,7-dihydroxynaphthalene was used in place of the 4,4'-dihydroxydiphenyl. Thus, there was obtained 11.3 g of a white polymer.

EXAMPLE 7

The procedure of Example 3 was repeated except that 7.5 g (0.0503 mole) of 2,6-dichloropyridine, 5.71 g (0.025 mole) of 2,2'-bis(4-hydroxyphenyl)propane, 4.65 g (0.025 mole) of 4,4'-dihydroxydiphenyl, 7.6 g (0.055 mole) of anhydrous potassium carbonate and 20 ml of 1,3-dimethyl-2-imidazolidinone were used in the reaction mixture. Thus, there was obtained 14 g of a white copolymer.

TABLE 1

| Example No. | $\eta inh$ (dl/g) | Tg (°C.) | Tm (°C.) | Td$_5$ (°C.) | Degree of crystallinity (%) |
|---|---|---|---|---|---|
| 1 | 1.66 | 115 | — | 462 | 0 |
| 2 | 0.35 | — | — | — | — |
| 3 | 1.49 | 145 | 252 | 445 | 38 |
| 4 | 1.27 | 73 | 251 | 436 | 40 |
| 5 | 0.38 | — | — | — | — |
| 6 | 0.85 | 113 | — | 445 | 13.4 |
| 7 | 1.25 | 110 | — | 442 | 0 |

TABLE 2

| Example No. | Load (kg) | Temperature (°C.) | Melt viscosity (poises) | Shear rate (sec$^{-1}$) |
|---|---|---|---|---|
| 1 | 20 | 240 | 2718 | 180 |
| 3 | 20 | 280 | 3487 | 141 |
| 4 | 30 | 260 | 3921 | 623 |
| 6 | 10 | 240 | 1084 | 226 |
| 7 | 100 | 170 | 4457 | 550 |

EXAMPLE 8

Into a reactor fitted with a stirrer and a water separator were charged 18.6 g (0.1 mole) of 4,4'-dihydroxydiphenyl, 11.7 g (0.2 mole) of 96% potassium hydroxide flakes, 100 ml of 1,3-dimethyl-2-imidazolidinone and 20 ml of benzene. Under the reflux of benzene, the water present in the reaction system was removed through the water separator. Then, 32.6 g (0.22 mole) of 2,6-dichloropyridine was added to the reaction mixture, and its internal temperature was kept at 120°–140° C. by heating the reaction mixture while passing nitrogen gas therethrough. Thus, the reaction was continued for 12 hours. On cooling, crystals precipitated from the reaction mixture. They were separated by filtration and recrystallized from 100 ml of fresh 1,3-dimethyl-2-imidazolidinone to obtain pure 4,4'-bis(6-chloro-2-pyridyloxy)diphenyl in the form of white needles. This product had a melting point of 103°–104.5° C. and the results of its elemental analysis were as follows:

| | C | H | N | Cl |
|---|---|---|---|---|
| Calcd. (%) for $C_{22}H_{16}N_2O_2Cl_2$ | 64.25 | 3.92 | 6.81 | 17.24 |
| Found (%) | 64.84 | 3.37 | 6.74 | 17.23 |

The pure 4,4'-bis(6-chloro-2-pyridyloxy)diphenyl thus obtained was used as a starting material in the following reaction.

Into a 100-ml flask fitted with a stirrer and a water separator were charged 11.42 g (0.05 mole) of purified 2,2'-bis(4-hydroxyphenyl)propane, 20.54 g (0.05 mole) of 4,4'-bis(6-chloro-2-pyridyloxy)diphenyl, 7.6 g (0.055 mole) of anhydrous potassium carbonate, 25 ml of 1,3-dimethyl-2-imidazolidinone and 20 ml of toluene. By heating this reaction mixture with stirring while passing nitrogen gas therethrough, water was azeotropically removed under the reflux of benzene for an hour. Subsequently, while the reflux was continued, the toluene was gradually expelled from the reaction system and the temperature was raised.

At a temperature of 170°–180° C., the reaction was continued for 3 hours with the removal and distillation of water by occational addition of toluene. Thereafter, the reaction was continued at 200° C. for 3 hours and then at 220° C. for 3 hours. On completion of the reaction, the resulting viscous resin solution was added dropwise to 800 ml of methanol stirred vigorously in a high-speed mixer. After completion of the addition, the stirring was continued for an additional 10 minutes and the resulting white precipitate was separated by filtration. This white precipitate was resuspended in 300 ml of a 70% aqueous solution of methanol, followed by stirring. Thereafter, the white precipitate was separated by filtration, washed with water and then dried to obtain a polymer.

EXAMPLES 9–17

Various 4,4'-bis(6-chloro-2-pyridyloxy) compounds were prepared in substantially the same manner as described in Example 8. Then, various polyether-pyridines were prepared by using these 4,4'-bis(6-chloro-2-pyridyloxy) compounds in combination with the respective dihydroxy compounds, bases and solvents shown in Table 3.

TABLE 3

Alternating Co-condensation Polyether-pyridines

| Example No. | Type of X*1 | Type of X*2 | Base | Solvent |
|---|---|---|---|---|
| 9 |  |  | Potassium carbonate/ sodium carbonate (1:1) | 1,3-Dimethyl-2-imidazolidinone |
| 10 | 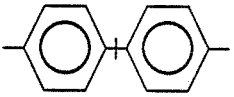 |  | Potassium carbonate | N—methylpyrrolidone |
| 11 |  |  | Potassium carbonate | 1,3-Dimethyl-2-imidazolidinone |
| 12 |  | 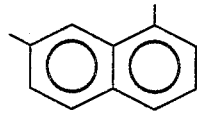 | Potassium carbonate | 1,3-Dimethyl-2-imidazolidinone |
| 13 |  |  | Sodium carbonate | Sulfolane |
| 14 | 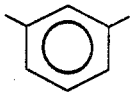 |  | Potassium carbonate | Sulfolane |
| 15 | 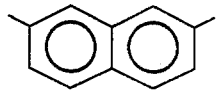 | 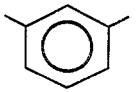 | Potassium carbonate | Dimethyl sulfoxide |
| 16 | 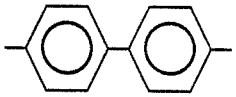 | 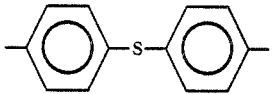 | Potassium carbonate | 1,3-Dimethyl-2-imidazolidinone |
| 17 | 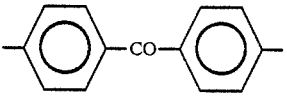 | 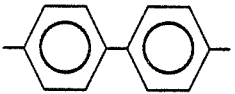 | Sodium carbonate | 1,3-Dimethyl-2-imidazolidinone |

| Example No. | Structure of polymer |
|---|---|
| 9 | 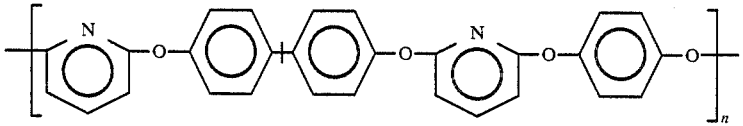 |
| 10 | 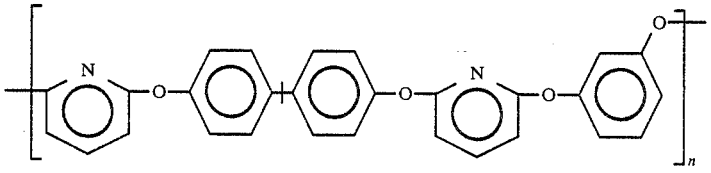 |

TABLE 3-continued
Alternating Co-condensation Polyether-pyridines

11 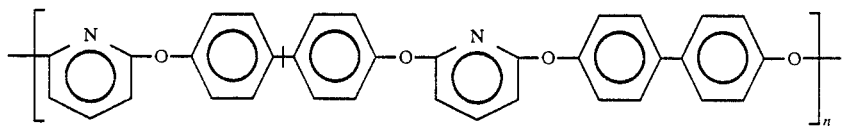

12 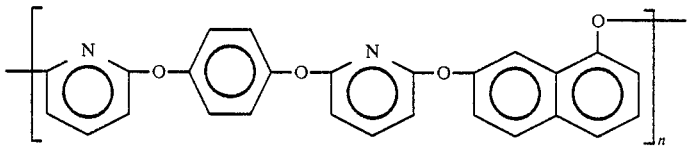

13 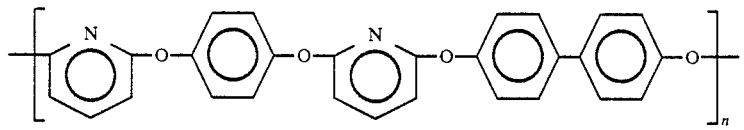

14 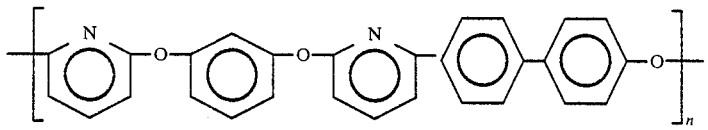

15 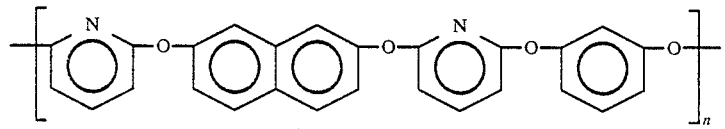

16 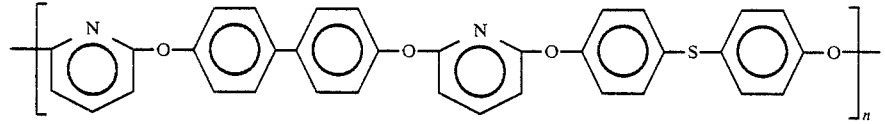

17 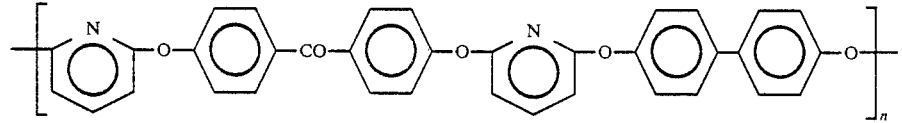

*[1]The type of X present in the bis(6-chloro-2-pyridyloxy) compound.
*[2]The type of X in the dihydroxy compound.

TABLE 4
Properties of Alternating Co-condensation Polyether-pyridines

| | | Results of thermal analysis | | | | Flow Characteristics | | |
|---|---|---|---|---|---|---|---|---|
| Example No. | ηinh (dl/g) | Tg (°C.) | Tm (°C.) | Td5 (°C.) | Degree of crystallinity (%) | Load (kg) | Temperature (°C.) | Melt viscosity (poises) | Shear rate (sec$^{-1}$) |
| 8 | 0.89 | 110 | — | 462 | 0 | 100 | 180 | 1600 | 1530 |
| 9 | 0.92 | 96 | — | 440 | 0 | 100 | 180 | 5000 | 490 |
| 10 | 0.96 | 86 | — | 443 | 0 | 100 | 180 | 5000 | 490 |
| 11 | 1.15 | 110 | — | 460 | 0 | 100 | 170 | 1950 | 1250 |
| 12 | 0.5 | 96 | — | 435 | 0 | 100 | 150 | 5580 | 439 |
| 13 | 0.83 | 103 | 195 | 468 | 21.2 | 100 | 200 | <1000 | >2500 |
| 14 | 1.25 | 83 | — | 460 | 0 | 100 | 200 | 1800 | 270 |
| 15 | 0.53 | 81 | — | 440 | 0 | 100 | 150 | 1300 | 1870 |
| 16 | 0.52 | 99 | — | 448 | 0 | 100 | 150 | 1300 | 190 |
| 17 | 1.39 | 180 | — | 450 | 0 | — | — | — | — |

What is claimed is:

1. A thermoplastic aromatic polyether-pyridine composed of repeating structural units of the general formula

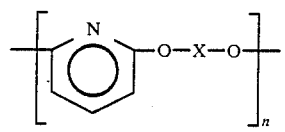 (1)

where X is a divalent radical selected from the group consisting of

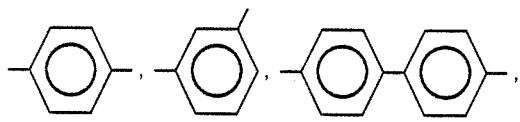

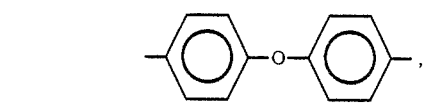

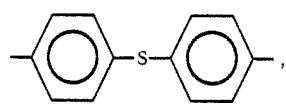

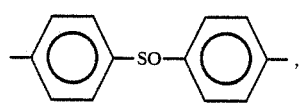

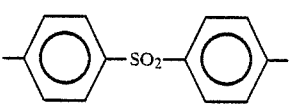

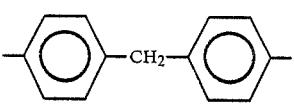

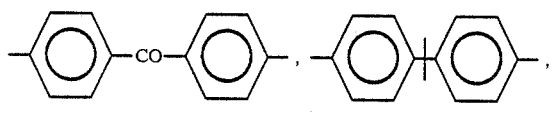

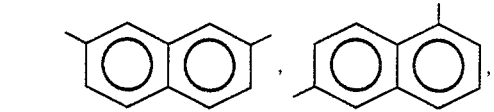

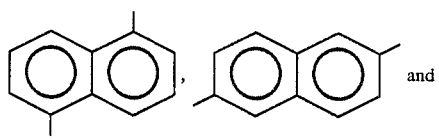

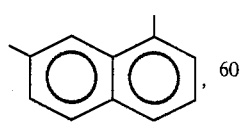

one or two of such divalent radicals are present in the molecule, and n represents a degree of polymerization and is a whole number of 10 or greater.

2. A thermoplastic aromatic polyether-pyridine as claimed in claim 1 which is composed of repeating structural units of the general formula

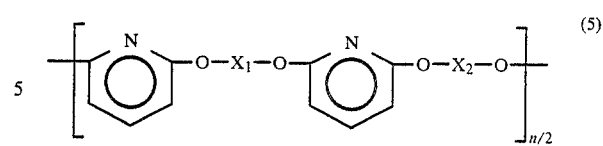 (5)

where $X_1$ and $X_2$ are divalent radicals selected form the group consisting of

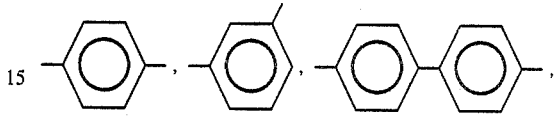

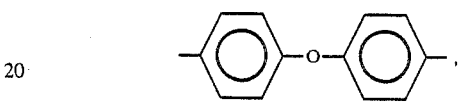

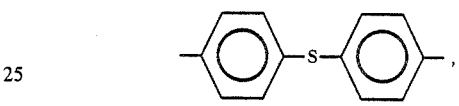

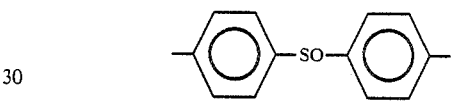

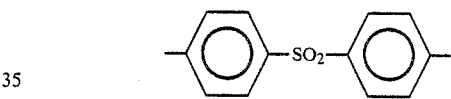

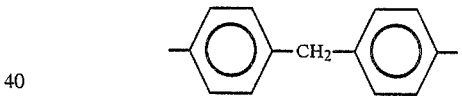

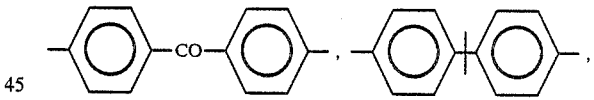

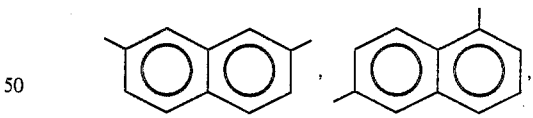

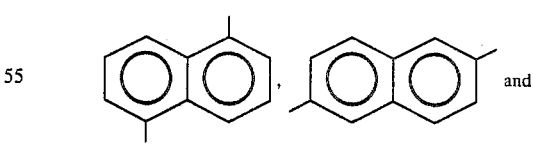

and a different from each other.

3. A process for preparing a thermoplastic aromatic polyether-pyridine composed of repeating structural units of the general formula

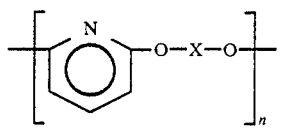 (1)

where X is a divalent radical selected from the group consisting of

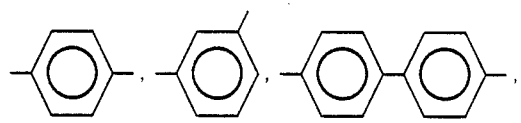

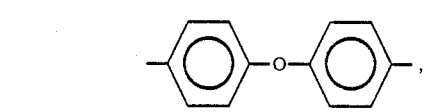

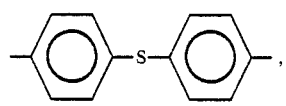

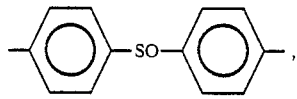

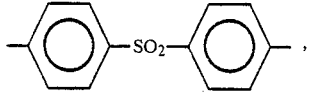

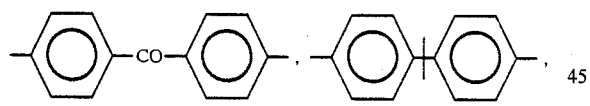

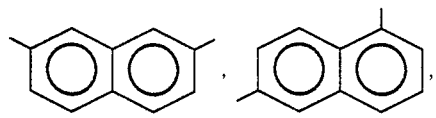

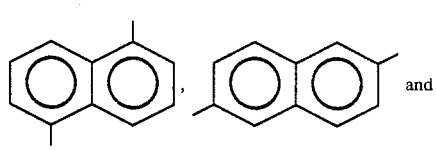

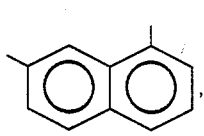, one or two of such divalent radicals are present in the molecule, and n represents a degree of polymerization and is a whole number of 10 or greater, which comprises (a) mixing a 2,6-dihalogenopyridine of the general formula

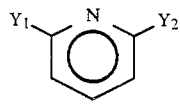 (2)

where $Y_1$ and $Y_2$ are chlorine, bromine or fluorine atoms and are the same or different, with one or two dihydroxy compounds of the general formula

HO—X—OH (3)

where X is a divalent radical selected from the group consisting of

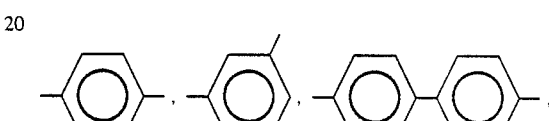

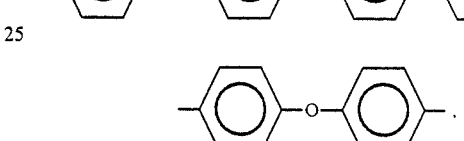

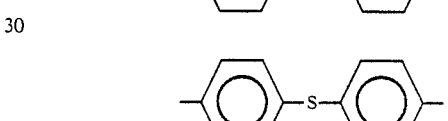

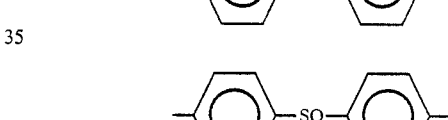

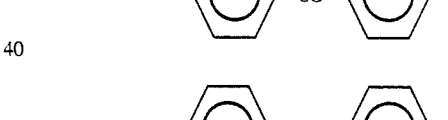

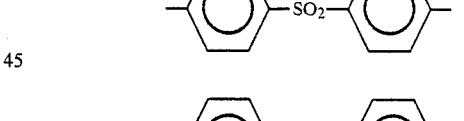

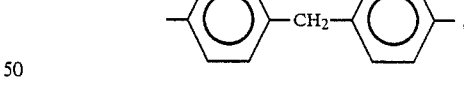

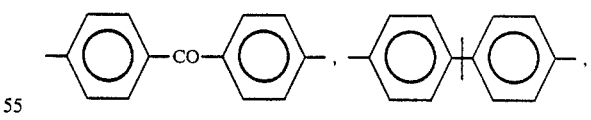

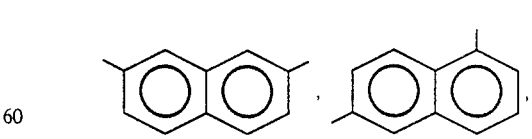

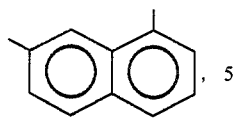

in a substantially equimolar ratio, and (b) effecting polycondensation of these reactants under substantially water-free conditions in the presence of an alkali metal carbonate or bicarbonate or an alkali metal hydroxide.

4. A process for preparing a thermoplastic aromatic polyetherpyridine composed of repeating structural units of the general formula

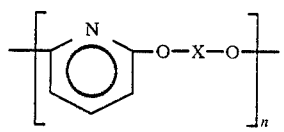 (1)

where X is a divalent radical selected from the group consisting of

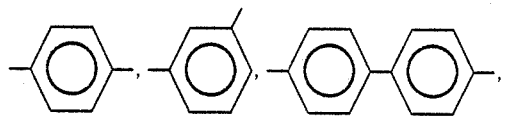

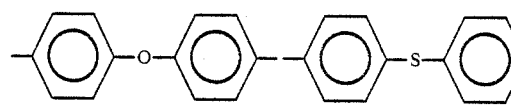

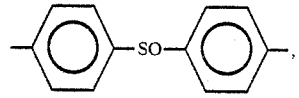

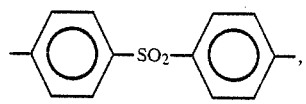

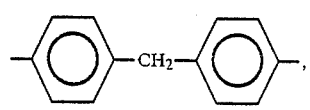

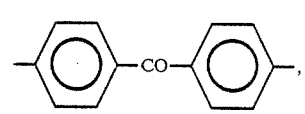

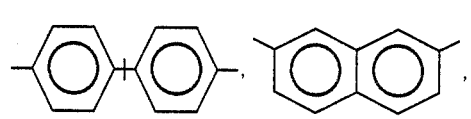

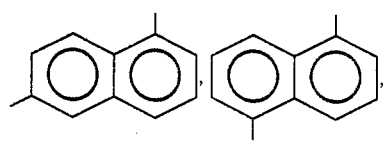

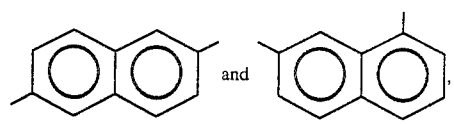

one of two of such divalent radicals are present in the molecule, and an represents a degree of polymerization and is a whole number of 10 or greater, which comprises (a) mixing a bis(6-chloro-2-pyridyloxy) compound of the general formula

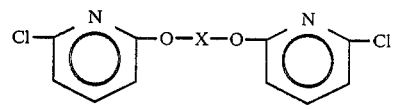 (4)

where X is a divalent radical selected from the group consisting of

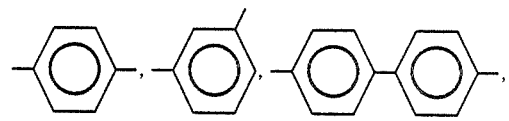

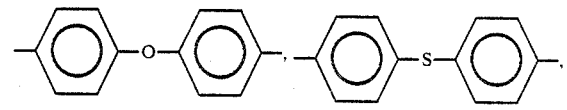

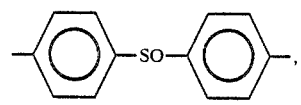

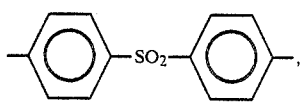

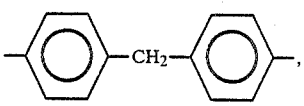

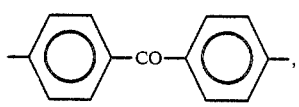

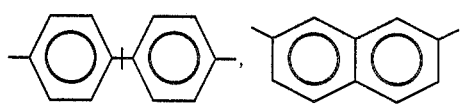

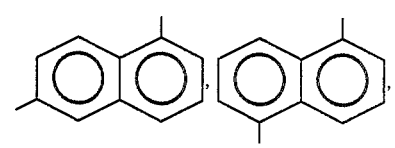

-continued

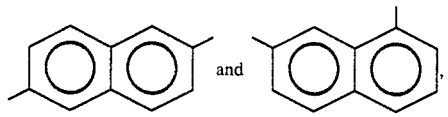

with a dihydroxy compound of the general formula

HO—X—OH           (3)

where X is a divalent radical selected from the group consisting of

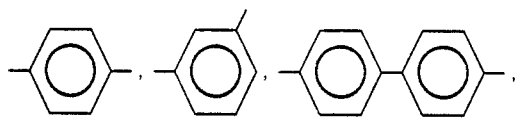

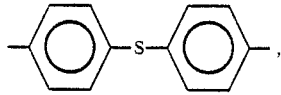

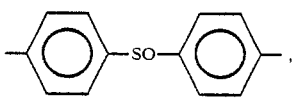

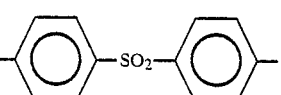

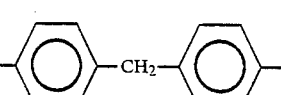

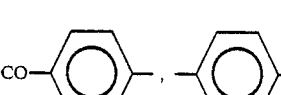

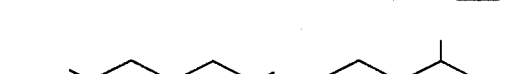

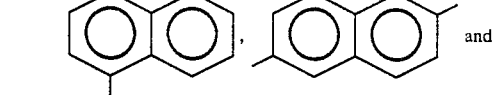

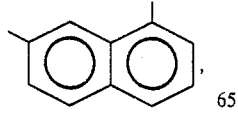

in a substantially equimolar ratio, and (b) effecting polycondensation of these reactants under substantially water-free conditions in the presence of an alkali metal carbonate or bicarbonate or an alkali metal hydroxide.

5. A process as claimed in claim 4 wherein the thermoplastic aromatic polyether-pyridine is composed of repeating structural units of the general formula

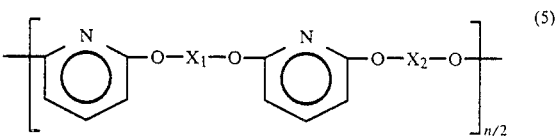         (5)

where $X_1$ and $X_2$ are divalent radicals selected from the group consisting of

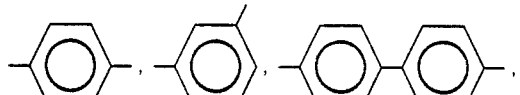

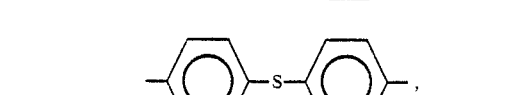

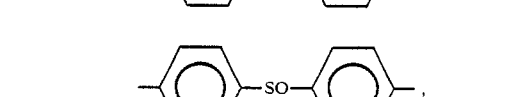

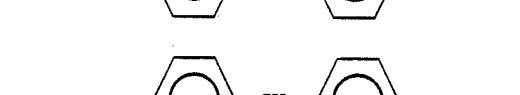

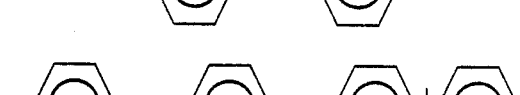

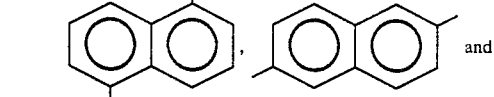

and are different from each other.

* * * * *